US010829429B2

(12) United States Patent
Chakraborty et al.

(10) Patent No.: US 10,829,429 B2
(45) Date of Patent: Nov. 10, 2020

(54) SYNTHESIS OF TRIETHYLENE GLYCOL BIS(2-ETHYLHEXANOATE)

(71) Applicant: Eastman Chemical Company, Kingsport, TN (US)

(72) Inventors: Sumit Chakraborty, Johnson City, TN (US); Steven J. Adams, Gray, TN (US); Robert Thomas Hembre, Johnson City, TN (US); Scott Donald Barnicki, Kingsport, TN (US); David Alan Jenkins, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/188,958

(22) Filed: Nov. 13, 2018

(65) Prior Publication Data
US 2020/0148619 A1 May 14, 2020

(51) Int. Cl.
*C07C 67/03* (2006.01)
*B01J 27/232* (2006.01)
*B01J 31/02* (2006.01)
*C07C 69/708* (2006.01)

(52) U.S. Cl.
CPC ............ *C07C 67/03* (2013.01); *B01J 27/232* (2013.01); *B01J 31/0212* (2013.01); *B01J 2531/46* (2013.01); *C07C 69/708* (2013.01)

(58) Field of Classification Search
None
See application file for complete search history.

(56) References Cited

U.S. PATENT DOCUMENTS

| 3,215,712 | A | 11/1965 | Hübel | |
|---|---|---|---|---|
| 5,892,102 | A | 4/1999 | Mikami et al. | |
| 2003/0176300 | A1* | 9/2003 | Kodali | C10M 101/04 508/452 |
| 2010/0317824 | A1* | 12/2010 | Thoen | C07C 67/03 528/361 |
| 2016/0137582 | A1* | 5/2016 | Frey | C07C 67/08 560/198 |
| 2016/0207871 | A1 | 7/2016 | Kubitschke et al. | |
| 2016/0297741 | A1 | 10/2016 | Janka et al. | |

FOREIGN PATENT DOCUMENTS

| EP | 2 308 824 A2 | 4/2011 |
|---|---|---|
| JP | 08-099933 A | 4/1996 |
| JP | H11-43463 A | 2/1999 |
| JP | 2001-220367 A | 8/2001 |
| WO | WO 2016/164195 A1 | 10/2016 |

OTHER PUBLICATIONS

Thermo Fisher Scientific product page for Acros organics 5.4M (30 wt%) solution in methanol, downloaded from https://www.fishersci.com/shop/products/sodium-methoxide-5-4m-30-wt-solution-methanol-acroseal-acros-organics-2/AC428361000 on Jul. 2, 2019 (Year: 2019).*
Office Action dated Jun. 10, 2019 received in co-pending U.S. Appl. No. 16/188,930.
Co-pending U.S. Appl. No. 16/188,930, filed Nov. 13, 2018; Chakraborty et al.
Co-pending U.S. Appl. No. 16/188,976, filed Nov. 13, 2018; Chakraborty et al.
Blum et al.; "Catalytically Reactive Ruthenium Intermediates in the Homogeneous Oxidation of Alcohols to Esters;" Israel Journal of Chemistry; vol. 24; 1984; pp. 144-148.
Blum et al.; "Catalytically Reactive ($\eta^4$-tetracyclone)(CO)$_2$(H)$_2$Ru and Related Complexes in Dehydrogenation of Alcohols to Esters;" Journal of Organometallic Chemistry; 1985; 282; pp. C7-C10.
Blum et al.; "Structure of "$\eta^4$-Ph$_4$C$_4$CO)(CO)$_3$Ru—a Catalyst Precursor in H-Transfer and Dehydrogenation Reactions of Alcohols;" Inorganica Chimica Acta; 1985; 97; pp. L25-L26.
Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.
Gianetti et al.; "Nitrous Oxide as a Hydrogen Acceptor for the Dehydrogenative Coupling of Alcohols;" Angew. Chem. Int. Ed.; 2016; 55; pp. 1854-1858.
Grigg et al.; "Oxidation of Alcohols by Transition Metal Complexes—IV;" Tetrahedron; 1981; vol. 37; No. 24; pp. 4313-4319.
Gunanathan et al.; "Applications of Acceptorless Dehydrogenation and Related Transformations in Chemical Synthesis;" Science; 2013; vol. 341; pp. 249.
Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.
Karmel et al.; "Mono(imidazoline-2-iminato) Actinide Complexes: Synthesis and Application in the Catalytic Dimerization of Aldehydes;" J. Am. Chem. Soc.; 2014; 136; pp. 17180-17192.
Khusnutdinova et al.; "Metal-Ligand Cooperation;" Angew. Chem. Int. Ed.; 2015; 54; pp. 12236-12273.
Kiran et al.; "Single-Step Conversion of Electron-Deficient Aldehydes into the Corresponding Esters in Aqueous Alcohols in the Presence of Iodine and Sodium Nitrite;" Synthesis; 2010; 2; pp. 276-282.
Kuriyama et al.; "Catalytic Hydrogenation of Esters. Development of an Efficient Catalyst and Processes for Synthesising (R)-1,2-Propanediol and 2-(l-Menthoxy)ethanol;" Org. ProcessRes. Dev.; 2012; 16; pp. 166-171.

(Continued)

*Primary Examiner* — Amy C Bonaparte
(74) *Attorney, Agent, or Firm* — Matthew W. Smith

(57) ABSTRACT

A process for the transesterification of methyl-2-ethylhexanoate with triethylene glycol to produce triethylene glycol di-2-ethylhexanoate is provided. In the process, methyl-2-ethylhexanoate is combined with triethylene glycol to form a first mixture. The first mixture is heated in the presence of a catalyst to form a second mixture comprising methanol and triethylene glycol di-2-ethylhexanoate. Methanol is separated from the second mixture to yield triethylene glycol di-2-ethylhexanoate. $Na_2CO_3$, $Cs_2CO_3$, $K_2CO_3$, $Rb_2CO_3$, sodium methoxide or titanium isopropoxide are suitable catalysts.

15 Claims, No Drawings

(56) References Cited

OTHER PUBLICATIONS

Lee et al.; "N-Heterocyclic Carbene Catalyzed Oxidative Macrolactonization: Total Synthesis of (+)-Dactyolide;" Angew. Chem. Int. Ed.; 2012; 51; pp. 5735-5738.
Murahashi et al.; "Ruthenium-Catalyzed Oxidative Transformation of Alcohols and Aldehydes to Esters and Lactones;" J. Org. Chem.; 1987; 52; pp. 4319-4327.
Murahasi et al.; "Ruthenium Catalyzed Transformation of Alcohols to Esters and Lactones;" Tetrahedron Letters; 1981; vol. 22; No. 52; pp. 5327-5330.
Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.
Rueping et al.; "Asymmetric oxidative Lewis base catalysis—unifying iminium and enamine organocatalysis with oxidations;" Chem. Commun.; 2012; 48; pp. 2201-2203.
Sarkar et al.; "NHC Catalyzed Oxidations of Aldehydes to Esters: Chemoselective Acylation of Alcohols in Presence of Amines;" J. Am. Chem. Soc.; 2010; 132; pp. 1190-1191.
Spasyuk et al.; "Acceptorless Dehydrogenative Coupling of Ethanol and Hydrogenation of Esters and Imines;" Organometallics; 2012; 31; pp. 5239-5242.
Spasyuk et al.; "From Esters to Alcohols and Back with Ruthenium and Osmium Catalysts;" Angew. Chem. Int. Ed.; 2012; 51; pp. 2772-2775.
Spasyuk et al.; "Chemoselective Hydrogenation of Carbonyl Compounds and Acceptorless Dehydrogenative Coupling of Alcohols;" J. Am. Chem. Soc.; 2015; 137; pp. 3743-3746.
Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.
Sumino et al.; "Carbonylation Reactions of Alkyl Iodides through the Interplay of Carbon Radicals and Pd Catalysts;" Acc. Chem. Res.; 2014; 47; pp. 1563-1574.
Toubiana et al.; "The true catalyst in hydrogen transfer reactions with alcohol donors in the presence of $RuCl_2(PPh_3)_3$ is ruthenium(0) nanoparticles;" Catal. Sci. Technol.; 2012; 2; pp. 1644-1653.
Trincado et al.; "Molecular catalysts for hydrogen production from alcohols;" Energy Environ. Sci.; 2014; 7; pp. 2464-2503.
Whittaker et al.; "Nickel-Catalyzed Dehydrogenative Cross-Coupling: Direct Transformation of Aldehydes into Esters and Amides;" Angew. Chem. Int. Ed.; 2015; 54; pp. 1312-1315.
Yang et al.; "Substitution of alcohols by N-nucleophiles via transition metal-catalyzed dehydrogenation;" Chem. Soc. Rev.; 2015; 44; pp. 2305-2329.
Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.
Zhang et al.; "Facile Conversion of Alcohols into Esters and Dihydrogen Catalyzed by New Ruthenium Complexes;" J. Am. Chem. Soc.; 2005; 127; pp. 10840-10841.
Office Action dated Jun. 21, 2019 received in co-pending U.S. Appl. No. 16/188,976.
Eberhardt et al.; "Dehydrogenative Coupling of Aldehydes with Alcohols Catalyzed by a Nickel Hydride Complex;" Organometallics; 2019; 38; pp. 1468-1478.
Johnson et al.; "(Cyclopentadienone)iron Shvo Complexes: Synthesis and Applications to Hydrogen Transfer Reactions;" Organometallics; 2013; 30; pp. 1859-1868.
Yang et al.; "New air-stable iron catalyst for efficient dynamic kinetic resolution of secondary benzylic and aliphatic alcohols;" Tetrahedron Letters; 58; 2017; pp. 2487-2489.
Notice of Allowance dated Dec. 19, 2019 received in co-pending U.S. Appl. No. 16/188,930.
Notice of Allowance dated Dec. 20, 2019 received in co-pending U.S. Appl. No. 16/188,976.
Baldino et al.; "Transfer Hydrogenation and Hydrogenation of Commercial-Grade Aldehydes to Primary Alcohols Catalyzed by 2-(Aminomethyl)pyridine and Pincer Benzo[h] quinoline Ruthenium Complexes;" Chemcatchem; vol. 8; No. 13; 2016; pp. 2279-2288.
Blum et al.; "H-transfer catalysis with $Ru_3(Co)_{12}$;" Tetrahedron Letters; vol. 22; No. 16; Jan. 1, 1981; pp. 1541-1544.
Funk et al.; "Synthesis and Catalytic Activity of (3,4-Diphenylcyclopentadienone) Iron Tricarbonyl Compounds in Transfer Hydrogenations and Dehydrogenations;" Organometallics; vol. 37; No. 7; Mar. 27, 2018; pp. 1133-1140.
Menashe et al.; "Catalytic disproportionation of aldehydes with ruthenium complexes;" Organometallics; vol. 10; No. 11; 1991; pp. 3885-3891.
Notification of Transmittal of the International Search Report and the Written Opinion of the International Searching Authority dated Feb. 21, 2020 received in International Application No. PCT/US2019/060822.
Notification of Transmittal of the International Search Report and the Written Opinion of the International Searching Authority dated Feb. 27, 2020 received in International Application No. PCT/US2019/060818.
Notification of Transmittal of the International Search Report and the Written Opinion of the International Searching Authority dated Feb. 27, 2020 received in International Application No. PCT/US2019/060814.

* cited by examiner

SYNTHESIS OF TRIETHYLENE GLYCOL BIS(2-ETHYLHEXANOATE)

FIELD OF THE INVENTION

The invention generally relates to the field of organic chemistry. It particularly relates to the transesterification of methyl-2-ethylhexanoate (M2EH) with triethylene glycol (TEG) to produce triethylene glycol di-2-ethylhexanoate (TEG-2EH also known as triethylene glycol bis(2-ethylhexanoate)).

BACKGROUND OF THE INVENTION

Triethyleneglycol di-2-ethylhexanoate (TEG-2EH) is a key plasticizer for the interlayers business. In particular, TEG-2EH is used in automotive, residential and commercial window applications. TEG-2EH can be produced by making 2-ethylhexanal (HEH) from the aldol condensation/hydrogenation of n-butyraldehyde. 2-ethylhexanal is oxidized to produce 2-ethylhexanoic acid (2EHacid). An excess of 2-ethylhexanoic acid is then condensed with triethylene glycol (TEG) to form TEG-2EH. However, this process for the production of TEG-2EH suffers from the disadvantages of multiple synthesis steps, multiple purification steps and relatively low yields.

An alternative approach, using aldehyde-alcohol-coupling-to-esters technology (AACE), such as the dehydrogenative coupling of 2-ethylhexanal (HEH) to methanol (MeOH) to produce methyl-2-ethylhexanoate (M2EH), followed by simple transesterification of methyl-2-ethylhexanoate with triethylene glycol to form TEG-2EH and methanol would alleviate the need for multiple synthesis steps and for the use of 2-ethylhexanoic acid.

The present invention addresses this need as well as others, which will become apparent from the following description and the appended claims.

SUMMARY OF THE INVENTION

The invention is as set forth in the appended claims.

In one embodiment the invention is a process for preparing triethyleneglycol di-2-ethylhexanoate comprising:
a) combining methyl-2-ethylhexanoate with triethylene glycol to form a first mixture;
b) heating the first mixture in the presence of a catalyst to form a second mixture comprising methanol and triethyleneglycol di-2-ethylhexanoate; and
c) separating methanol from the second mixture to yield triethyleneglycol di-2-ethylhexanoate.

In another embodiment the invention is a process for preparing triethyleneglycol di-2-ethylhexanoate comprising:
a) combining methyl-2-ethylhexanoate with triethylene glycol to form a first mixture;
b) heating the first mixture at a temperature of about 100° C. to about 180 C for about 2 hours to about 8 hours in the presence of a catalyst selected from the group $Na_2CO_3$, $Cs_2CO_3$, $K_2CO_3$, $Rb_2CO_3$, sodium methoxide or titanium isopropoxide to form a second mixture comprising methanol and TEG-2EH; and
c) separating methanol from the second mixture to yield TEG-2EH.

DETAILED DESCRIPTION OF THE INVENTION

As used herein the following terms have the meaning as defined below:

The term "M2EH" refers to methyl-2-ethylhexanoate.

The term "TEG" refers to triethylene glycol.

The term "TEG-2EH" refers to triethylene glycol di-2-ethylhexanoate.

The term "MeOH refers to methanol.

The term "Ti(OiPr)$_4$" refers to titanium isopropoxide (Ti[OCH(CH$_3$)$_2$]$_4$)

The abbreviation "wt %" means weight percent.

The abbreviation "mol %" means mole percent.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 0 to 100 is intended to describe and include all values within the range including sub-ranges such as 0.1 to 99.9, 1 to 99, 50-100, 60 to 90 and 70 to 80.

It has been surprisingly discovered that an efficient method to form a variety of methyl esters is via direct coupling of oxo aldehydes with methanol in the presence of Shvo's catalyst (Equation (1)).

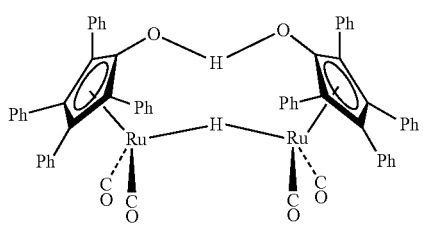

Shvo's Catalyst

Shvo's catalyst (1-Hydroxytetraphenyl-cyclopentadienyl (tetraphenyl-2,4-cyclopentadien-1-one)-mu-hydrotetracarbonyldiruthenium(II)) is available commercially from Millipore Sigma.

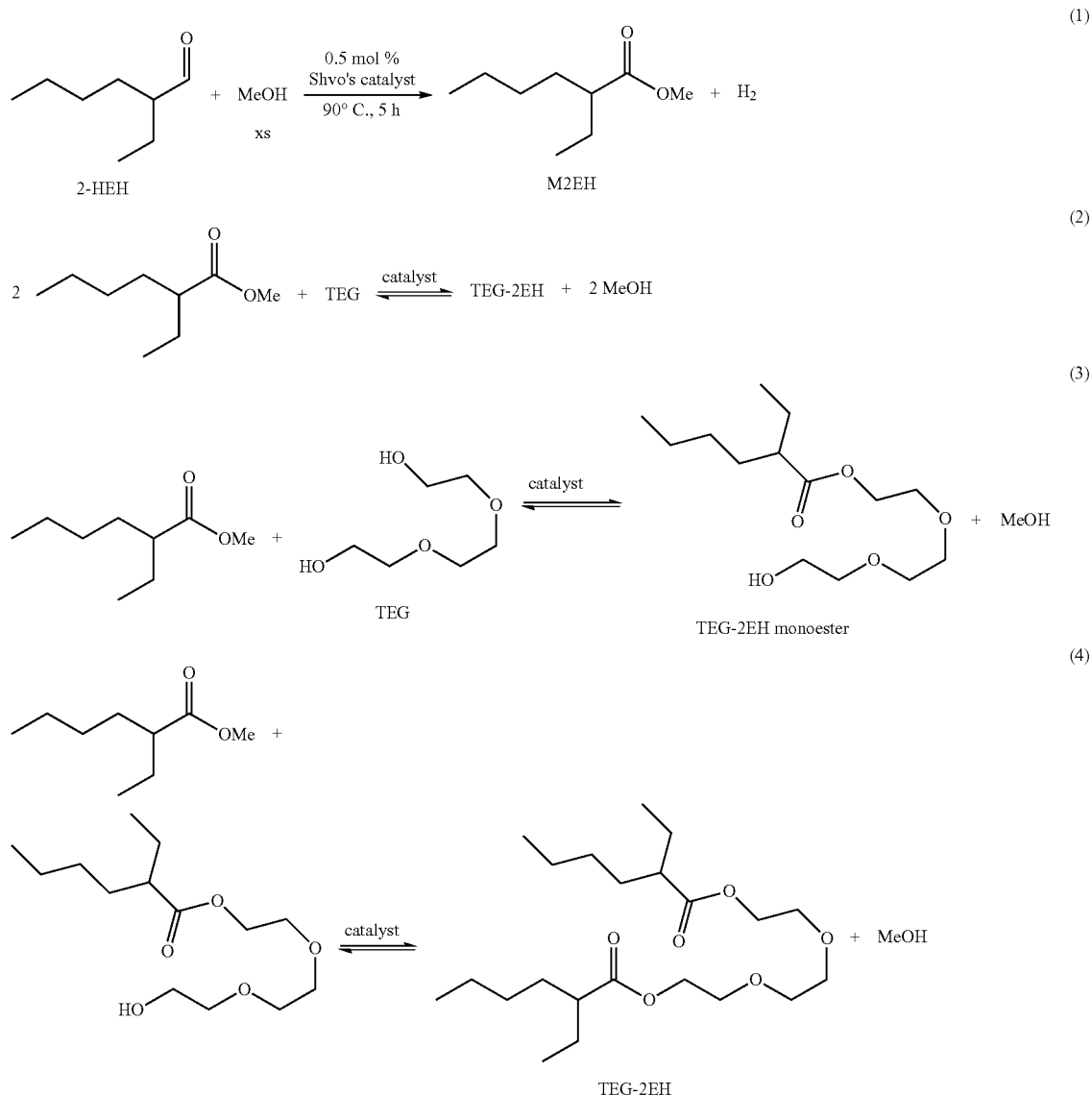

The yields and selectivities for these reactions were found to be excellent and generally fall within 95-99%. Of particular interest, is the reaction between 2-ethylhexanal and methanol to produce methyl-2-ethylhexanoate in 99.5% yield and high selectivity. This discovery has allowed us to consider a new route that employs a transesterification reaction between methyl-2-ethylhexanoate and triethylene glycol to produce triethylene glycol di-2-ethylhexanoate (TEG-2EH) as the product (Equation (2)). Low-boiling methanol is the sole byproduct of this reaction and therefore it is possible to thermodynamically drive the reaction to completion by continuously removing methanol from the reaction system.

We examined a variety of readily available catalysts to carry out the transesterification reaction between methyl-2-ethylhexanoate and triethylene glycol. The formation of TEG-2EH occurs in two steps: one equivalent of methyl-2-ethylhexanoate reacts with triethylene glycol to afford TEG-2EH monoester (Equation (3)) and the second equivalent of methyl-2-ethylhexanoate further reacts with the monoester to yield desired TEG-2EH diester (Equation (4)).

In some embodiments of this invention suitable catalysts include carbonate salts. In some embodiments of this invention, suitable catalysts include $Na_2CO_3$, $Cs_2CO_3$, $K_2CO_3$, $Rb_2CO_3$, sodium methoxide and titanium isopropoxide and mixtures thereof.

The temperature conducive for the TEG-2EH reaction may range, for example, from 100 to 180° C., 105 to 180° C., 110 to 180° C., 120 to 180° C., 125 to 180° C., 130 to 180° C., 135 to 180° C., 140 to 180° C., 100 to 175° C., 100 to 170° C., 100 to 165° C., 120 to 165° C., 125 to 165° C., 130 to 165° C., or 135 to 165° C.

The pressure at which the transesterification reaction may be carried out is not particularly limiting. For example, the pressure may range from atmospheric to 2 MPa. The reaction may be performed in an open reactor where the produced methanol may be withdrawn as the reaction proceeds. Alternatively, the reaction may be performed in a sealed reactor where the produced methanol remains in the reactor.

Preferably, the transesterification reaction is carried out in the absence of water.

The transesterification reaction may be conducted in the presence or absence of an organic solvent. Suitable solvents include aromatic and alkylaromatic solvents such as benzene, toluene and or xylenes, $C_9$-$C_{11}$ aromatics mixtures, substituted aromatics such as anisole, benzonitrile, or diphenyl ether, ethers of ethylene glycol such as diglyme, triglyme, or tetraglyme. Cyclic ethers such as tetrahydrofuran or dioxane may also be used. Saturated hydrocarbons such as cyclohexane, hexanes, heptane or octanes or chlorinated hydrocarbons such as chlorobenzene, dichlorobenzenes, dichloroethane, trichloroethylene and the like may also be used. Carboxylic acids, esters or alcohols are not preferred as they can complicate transesterification equilibria. Likewise, carboxylic amide solvents such as dimethyl acetamide or dimethyl formamide are also not preferred.

The transesterification reaction can take place with catalyst loadings of about 1 to 5 mole percent.

Methanol is readily separated from the reaction liquids by distillation, condensed and purified for alternative uses. These operations may be carried out in a batch or continuous mode.

The TEG-2EH recovered from the methanol TEG-2EH reaction mixture may be washed with water to remove the catalyst.

The process according to the invention can produce TEG-2EH with yields of at least 90%, at least 95% or at least 99%. The reaction times in which these yields may be achieved include, 8 hours or less, 7 hours or less, 6 hours or less, 5 hours or less, 4 hours or less, 3 hours or less, 2 hours or less, or 1 hour or less.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

This invention can be further illustrated by the following examples of preferred embodiments thereof, although it will be understood that these examples are included merely for purposes of illustration and are not intended to limit the scope of the invention unless otherwise specifically indicated.

EXAMPLES

Synthesis of methyl-2-ethylhexanoate

Anhydrous methanol (47.4 mole, 1523 grams) was added to a 5 L vessel and brought to 3.5° C. while stirring under a $N_2$ sparge. N-propanol (250 mL) was added to the collection trap and placed in a dry ice Dewar. 2-ethylhexanoyl chloride (1.46 mole, 237.5 grams) was added to a funnel and added dropwise to methanol under positive $N_2$ pressure over 20 min. Upon addition of all of the 2-ethylhexanoyl chloride (8.76 mole, 1425 grams) the vessel was allowed to stir overnight at room temperature under $N_2$ sparge. Half of the reaction mixture was transferred to a 5 L separatory funnel and washed twice with 2 L deionized water. This step was repeated, and the remaining mixture and all organics were transferred to a 3 L three neck flask equipped with thermowell, glass stopper, ten plate older Shaw column with L/L distillation head with magnetic reflux arm, condenser, and fraction take off arm. The mixture was brought to reflux at 135 torr and a reflux rate of 2. After discarding the first ten percent, methyl-2-ethylhexanoate (99.8% purity by GC) was collected.

Example 1. Brönsted Acid-Catalyzed Transesterification Between M2EH and TEG

A four-neck round-bottom flask equipped with a magnetic stirrer, N2 purge line, sampling port and a condenser was charged with methyl-2-ethylhexanoate (0.284 mole, 10 eq, 45 gram), TEG (0.0284 mole, 4.27 gram), and an acid catalyst (1.42 millimole, 0.270 gram). The resulting two-phase mixture was heated using a pre-heated oil-bath. As the reaction progressed, the two-phase system began to disappear, and a dark brown colored one-phase solution formed. This reaction mixture was analyzed by gas chromatography and weight percent values for different analytes were obtained from GC analysis. A Brönsted acid, p-toluenesulfonic acid (PTSA), catalyzed the formation of TEG-2EH. When methyl-2-ethylhexanoate and TEG were mixed in a relative mole ratio of 10:1 and the resulting mixture was heated to 138° C. for 6 hours in the presence of 5 mole % of PTSA, TEG-2EH was produced in a high yield (96.3 wt %) and 3.7 wt % of monoester was also generated (Table 1, Run 1). The color of the resulting solution turned dark brown during the course of 6 hours. Note that it is important to produce lightly colored TEG-2EH in order to avoid downstream bleaching process. Furthermore, when PTSA loading was decreased from 5 mol % to 1 mol %, the reactivity dropped significantly and only 52.1 wt % of TEG-2EH was produced after 6 hours. When methyl-2-ethylhexanoate was reacted in the presence of excess of TEG, TEG-2EH monoester was produced exclusively after 4 hours (Run 2). Other Brönsted acids such as 2-ethylhexanoic acid (2-HOEH), and phenol (PhOH) failed to catalyze the transesterification reaction (Runs 3 and 4).

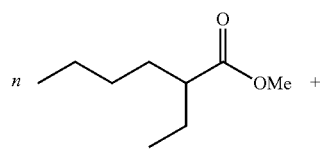

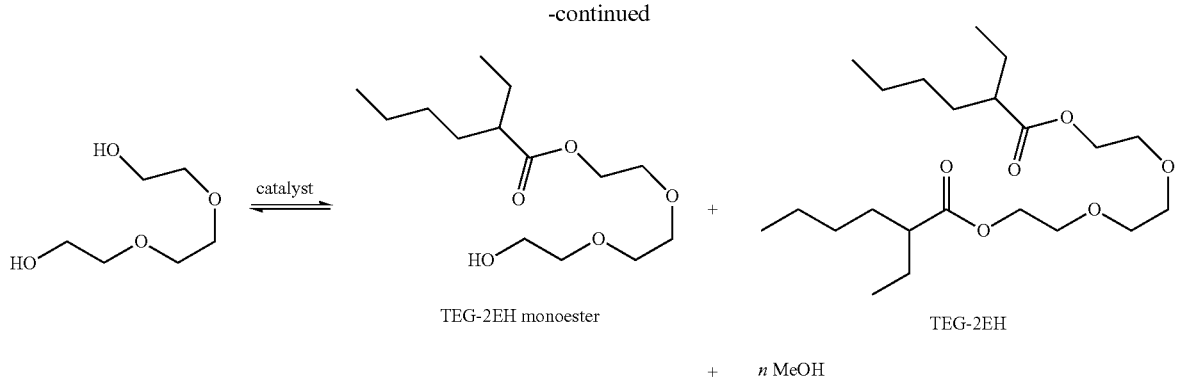

TABLE 1

Reactivity of Brönsted Acid Catalysts.

| Run | M2EH:TEG | Catalyst (loading) | Time (h) | Temp. (° C.) | Conv. (%) | TEG-2EH Mono (wt %) | TEG-2EH (wt %) |
|---|---|---|---|---|---|---|---|
| 1 | 10:1 | PTSA 5 mol % | 6 | 138 | 90 | 3.72 | 96.28 |
| 2 | 1:0 | PTSA 5 mol % | 4 | 138 | 100 | 100 (exclusive) | — |
| 3 | 10:1 | 2-HOEH 5 mol % | 22 | 138 | 0 | 0 | 0 |
| 4 | 10:1 | PhOH 5 mol % | 24 | 138 | 0 | 0 | 0 |

Example 2. Brönsted Base-Catalyzed Transesterification Between M2EH and TEG

As thermal degradation of Brönsted acid catalysts posed challenges, we next turned our attention to Brönsted bases (Table 2). A four-neck round-bottom flask equipped with a magnetic stirrer, N₂ purge line, sampling port and a condenser was charged with methyl-2-ethylhexanoate (0.284 mole, 10 eq, 45 gram), TEG (0.0284 mole, 4.27 gram), and a base catalyst (1.41 millimoel, 0.0767 gram). The resulting two-phase mixture was heated using a pre-heated oil-bath. As the reaction progressed, the two-phase system began to disappear, and a yellow solution resulted. This reaction mixture was analyzed by gas chromatography and weight percent values for different analytes were obtained from GC analysis. When 5 mol % of NaOMe was employed, both TEG-2EH monoester and TEG-2EH were produced with a relative wt % ratio of 69:100 after 6 hours at 138° C. (Run 5). After 22 hours, the relative ratio between monoester and TEG-2EH changed to 56:100 and the color of the solution remained faint yellow.

Although NaOMe showed reactivity, it proceeded with a much slower rate than PTSA.

Example 3. Ti or Ru-Catalyzed Transesterification Between M2EH and TEG

A four-neck round-bottom flask equipped with a magnetic stirrer, N₂ purge line, sampling port and a condenser was charged with methyl-2-ethylhexanoate (0.0852 mole, 3 eq), TEG (0.0284 mole, 4.27 gram), and a Ti or Ru catalyst (1.41 millimole). The resulting two-phase mixture was heated using a pre-heated oil-bath. As the reaction progressed, the two-phase system began to disappear, and a yellow solution resulted. This reaction mixture was analyzed by gas chromatography and weight percent values for different analytes were obtained from GC analysis. With 1 mol % of Cs₂CO₃, quantitative conversion of TEG was achieved and TEG-2EH was produced exclusively (Run 7, Table 2). This reaction was carried out at 160° C. for 4 hours with a slow nitrogen purge to remove methanol from the system. Only a trace amount of TEG-2EH monoester was detected by GC.

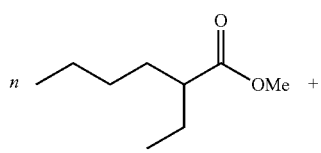

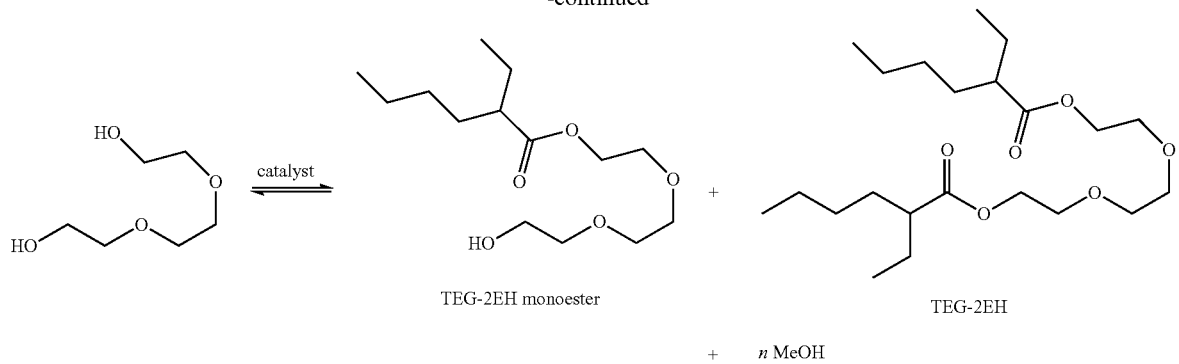

TEG-2EH monoester     TEG-2EH

+ *n* MeOH

TABLE 2

Catalytic Reactivity of Brönsted Bases.[a]

| Run | M2EH:TEG | Catalyst (loading) | Time (h) | Temp. (° C.) | Conv. (%) | TEG-2EH Mono (wt %) | TEG-2EH (wt %) |
|---|---|---|---|---|---|---|---|
| 5 | 10:1 | NaOMe 5 mol % | 6 | 138 | ? | 40.97 | 59.03 |
| 6 | 10:1 | NaOMe 5 mol % | 22 | 138 | 98.34 | 35.92 | 64.08 |
| 7 | 3:1 | Cs₂CO₃ 2 mol % | 4 | 160 | 100 | <0.1 | >99.9 |
| 8 | 3:1 | K₂CO₃ 2 mol % | 4 | 160 | 100 | 0.04 | 99.96 |

Example 4. K2CO3 (1 mol %), a Carbonate Analogue, was Employed as the Catalyst A four-neck round-bottom flask equipped with a magnetic stirrer, N₂ purge line, sampling port and a condenser was charged with methyl-2-ethylhexanoate (2.022 mole, 3.03 eq, 320 gram), TEG (0.667 mole, 100 gram), and K2CO3 (13.32 millimole, 1.841 gram). The resulting two-phase mixture was heated using a pre-heated oil-bath. As the reaction progressed (continuous MeOH removal using a distillation head), the two-phase system began to disappear, and a yellow solution resulted. This reaction mixture was analyzed by gas chromatography and weight percent values for different analytes were obtained from GC analysis. This reaction yielded >99 wt % of TEG-2EH after 3.5 hour (Run 8, Table 2)

To demonstrate the feasibility of scaling up this reaction, we carried out the K₂CO₃-catalyzed transestification reaction in a liter scale and successfully reproduced the synthesis of TEG-2EH under such conditions. K₂CO₃ and Cs₂CO₃-catalyzed reactions produced yellowish crude product and when passed through a Celite or Sillica Gel column, the color of the filtrate turned out to be faintly yellow. This indicates that a significant amount of color bodies could be removed by simply filtering the crude product through these materials. As carbonate salts are water soluble and TEG-2EH is insoluble in water, washing of the crude mixture with water could be used as a catalyst separation method.

Example 5

In addition to Brönsted acids and bases, we have also investigated the transesterification reaction in the presence of titanium isopropoxide and Shvo's catalyst (Table 3). While Shvo's complex showed no catalytic activity (Run 9), Ti(OiPr)₄ catalyst exhibited excellent reactivity under moisture-free conditions. When 2.7 mol % of Ti(OiPr)₄ was employed, TEG-2EH was produced with a high yield (98.9 wt %) and selectivity after 6 hours at 138° C. (Run 10). Best catalytic activity was observed when the titanium catalyst was added at the reaction temperature 138° C. As expected, when wet TEG was used in this reaction, Ti(OiPr)₄ reacted with water to form a white residue and the respective yield of TEG-2EH was much lower after 6 h (Run 11).

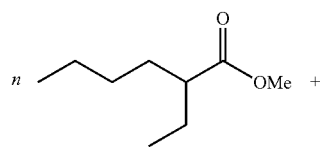

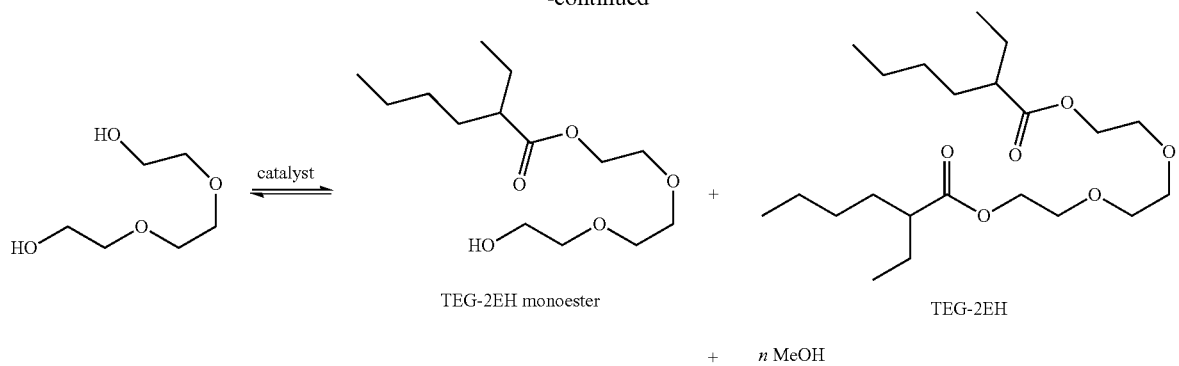

TEG-2EH monoester

TEG-2EH

+ n MeOH

TABLE 3

Reactivity of Ti(OiPr)$_4$ and Shvo's Catalyst.[a]

| Run | M2EH: TEG | Catalyst (loading) | Time (h) | Temp. (° C.) | Conv. (%) | TEG-2EH Mono (wt %) | TEG-2EH (wt %) |
|---|---|---|---|---|---|---|---|
| 9 | 3:1 | Shvo 5 mol % | 24 | 160 | <5 | 0 | 0 |
| 10 | 3:1 | Ti(OiPr)$_4$ 2.7 mol % | 6 | 138 | 100 | 1.1 | 98.9 |
| 11[a] | 3:1 | Ti(OiPr)$_4$ 2.7 mol % | 6 | 138 | 27 | 25.8 | 1.2 |

[a]10 wt % of water added to TEG.

Best catalytic results have been observed when anhydrous K$_2$CO$_3$ was used as the catalyst. With 2 mol % of K$_2$CO$_3$ catalyst and a 3:1 mixture of M2EH and TEG, TEG-2EH was produced with a high yield (98.9 wt %) and selectivity after 3.5 hours at 160° C. Only a trace amount of TEG-2EH monoester (0.03 wt %) was detected under this condition. Cs$_2$CO$_3$ and Ti(OiPr)$_4$ also turned out to be effective catalysts for this reaction.

In summary, we have discovered that carbonate salts, and in particular, K$_2$CO$_3$, efficiently catalyzes the transesterification reaction between methyl-2-ethylhexanoate and TEG to produce TEG-2EH in unprecedentedly high yields and selectivities under mild conditions. Cs$_2$CO$_3$ and Ti(OiPr)$_4$ are also effective catalysts for this transformation. Successful employment of carbonate salts offers simple catalyst separation procedures including washing the product with water.

In the specification, there have been disclosed certain embodiments of the invention and, although specific terms are employed, they are used in a generic and descriptive sense only and not for purposes of limitation, the scope of the invention being set forth in the following claims.

We claim:
1. A process for preparing triethyleneglycol di-2-ethylhexanoate comprising:
 a) combining methyl-2-ethylhexanoate, triethylene glycol, and a catalyst to form a first mixture;
 b) heating the first mixture to form a second mixture comprising methanol and triethyleneglycol di-2-ethylhexanoate; and
 c) separating methanol from the second mixture to yield triethyleneglycol di-2-ethylhexanoate wherein the catalyst is a Group I carbonate salt, and wherein the triethyleneglycol di-2-ethylhexanoate yield is at least 90%.

2. The process of claim 1 wherein the catalyst is selected from the group consisting of Na$_2$CO$_3$, Cs$_2$CO$_3$, K$_2$CO$_3$, and Rb$_2$CO$_3$.

3. The process of claim 1 wherein step b) is conducted at a temperature of about 100° C. to about 180° C. for about 2 hours to about 8 hours.

4. The process of claim 1 further comprising the step of washing the catalyst from said triethyleneglycol di-2-ethylhexanoate with water after step c).

5. The process of claim 1 wherein the molar ratio of methyl-2-ethylhexanoate to triethylene glycol in said first mixture is from 1:1 to 3:1.

6. The process of claim 1 wherein the molar amount of the catalyst in said first mixture is from about 1 mole percent to about 5 mole percent.

7. A process for preparing triethyleneglycol di-2-ethylhexanoate (TEG-2EH) comprising:
 a) combining methyl-2-ethylhexanoate, triethylene glycol, and a catalyst selected from the group consisting of Cs$_2$CO$_3$ and K$_2$CO$_3$ to form a first mixture;
 b) heating the first mixture at a temperature of about 100° C. to about 180° C. for about 2 hours to about 8 hours to form a second mixture comprising methanol and TEG-2EH; and
 c) separating methanol from the second mixture to yield TEG-2EH
wherein the TEG-2EH yield is at least 90%.

8. The process of claim 7 further comprising the step of washing the catalyst from said triethyleneglycol di-2-ethylhexanoate with water after step c).

9. The process of claim 7 wherein the molar ratio of methyl-2-ethylhexanoate to triethylene glycol in said first mixture is from 1:1 to 3:1.

10. The process of claim 7 wherein the molar amount of the catalyst in said first mixture is from about 1 mole percent to about 5 mole percent.

11. The process of claim 7 wherein step b is conducted at a temperature of about 135° C. to about 165° C.

12. A process for preparing triethyleneglycol di-2-ethylhexanoate comprising:
   a) combining methyl-2-ethylhexanoate, triethylene glycol, and a catalyst to form a first mixture;
   b) heating the first mixture form a second mixture comprising methanol and triethyleneglycol di-2-ethylhexanoate; and
   c) separating methanol from the second mixture to yield triethyleneglycol di-2-ethylhexanoate;

wherein said catalyst is selected from the group consisting of $Na_2CO_3$, $Cs_2CO_3$, and $K_2CO_3$, and wherein the triethyleneglycol di-2-ethylhexanoate yield is at least 90%.

13. The process of claim 12 wherein step b) is conducted at a temperature of about 100° C. to about 180° C. for about 2 hours to about 8 hours.

14. The process of claim 12 further comprising the step of washing catalyst from said triethyleneglycol di-2-ethylhexanoate with water after step c).

15. The process of claim 12 wherein the molar ratio of methyl-2-ethylhexanoate to triethylene glycol in said first mixture is from 1:1 to 3:1.

\* \* \* \* \*